United States Patent [19]
Kuroiwa et al.

[11] Patent Number: 5,296,819
[45] Date of Patent: Mar. 22, 1994

[54] POLYMER CAPACITATIVE MOISTURE SENSITIVE DEVICE COMPRISING HEATING MEANS

[75] Inventors: Takaaki Kuroiwa; Tooru Abe; Tetsuya Miyagishi, all of Kanagawa, Japan

[73] Assignee: Yamatake-Honeywell Co., Ltd., Japan

[21] Appl. No.: 903,000

[22] Filed: Jun. 23, 1992

[30] Foreign Application Priority Data

Jun. 25, 1991 [JP] Japan .................... 3-179006

[51] Int. Cl.$^5$ ............... G01N 25/56; G01R 27/26
[52] U.S. Cl. .................... 324/670; 324/664; 324/669; 324/685; 324/689; 73/335.04; 361/286
[58] Field of Search ............ 324/663, 664, 669, 670, 324/684, 685, 689; 73/335.02, 335.04; 361/286

[56] References Cited

U.S. PATENT DOCUMENTS

| | | | |
|---|---|---|---|
| 3,287,974 | 11/1966 | Ciemochowski | 73/335.04 |
| 4,393,434 | 7/1983 | Imai et al. | 73/335.04 |
| 4,737,707 | 4/1988 | Mori et al. | 324/689 |
| 4,898,476 | 2/1990 | Herrmann et al. | 324/664 X |
| 5,050,434 | 9/1991 | Demisch | 73/335.04 |
| 5,069,069 | 12/1991 | Miyagishi et al. | 73/335.04 |
| 5,143,696 | 9/1992 | Haas et al. | 324/663 X |
| 5,161,085 | 11/1992 | Sakai et al. | 361/286 |

Primary Examiner—Kenneth A. Wieder
Assistant Examiner—Glenn W. Brown
Attorney, Agent, or Firm—Blakely, Sokoloff, Taylor & Zafman

[57] ABSTRACT

A moisture sensitive device includes a polymer capacitive moisture sensitive element and a heater. The polymer capacitive moisture sensitive element is formed by sequentially stacking a lower electrode, a moisture sensitive film made of an organic polymer resin material, and an upper electrode on an insulating substrate. The heater serves to heat the moisture sensitive film to restore the original characteristics thereof.

3 Claims, 19 Drawing Sheets

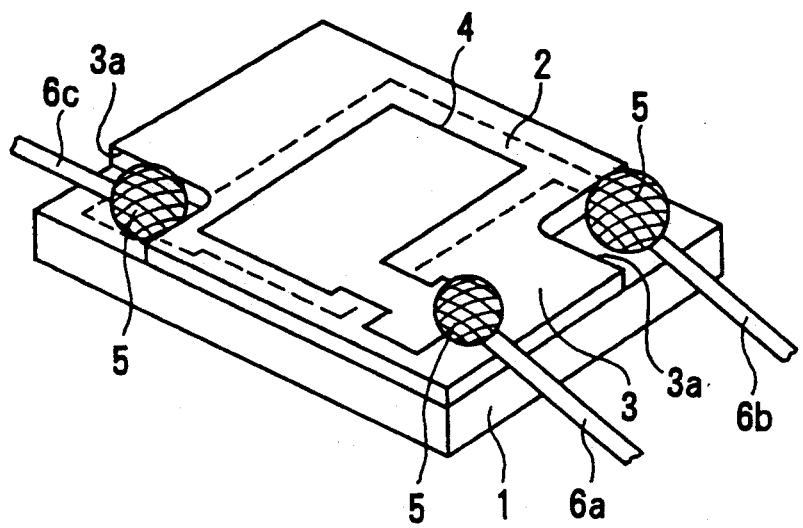
F I G. 5A
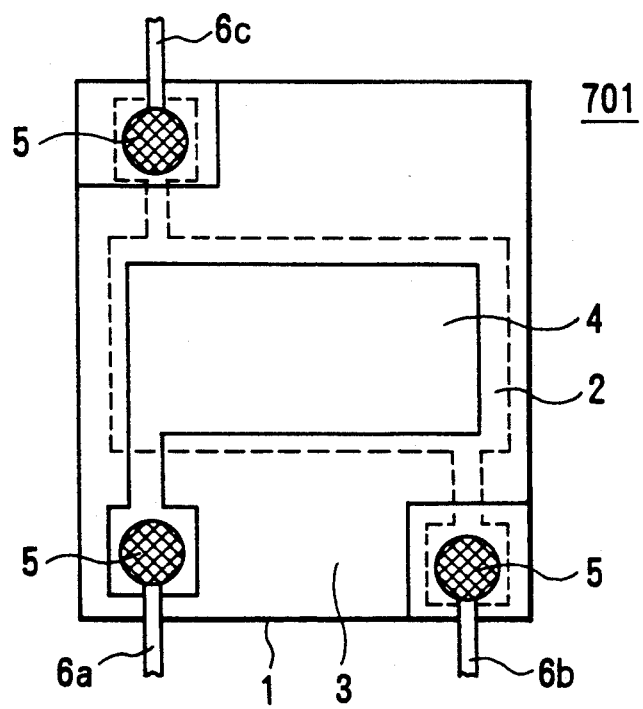
F I G. 5B

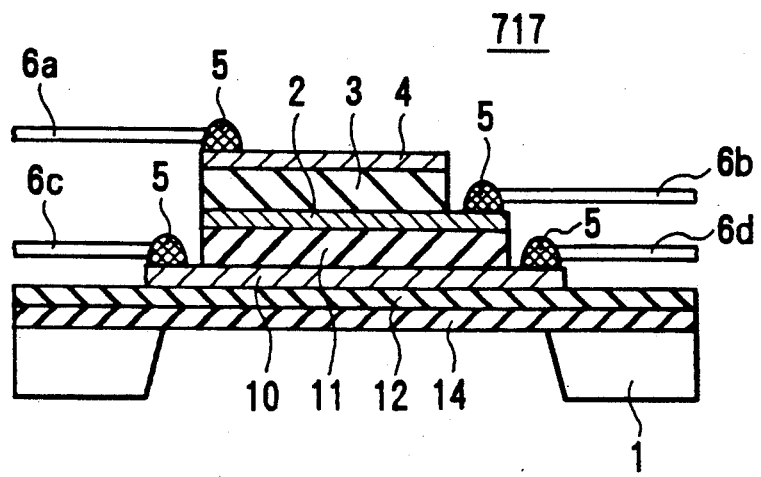
F I G. 29A
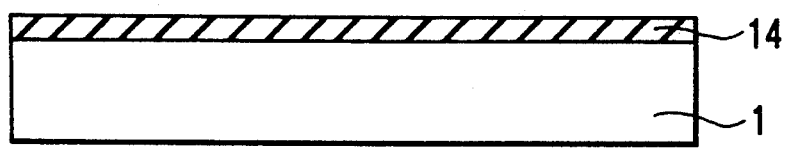
F I G. 29B
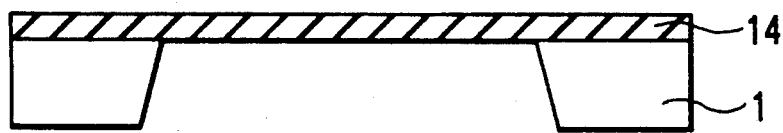
F I G. 29C

POLYMER CAPACITATIVE MOISTURE SENSITIVE DEVICE COMPRISING HEATING MEANS

BACKGROUND OF THE INVENTION

The present invention relates to a moisture sensitive device using a moisture sensitive element consisting of an organic polymer resin as a moisture sensitive material.

If a conventional polymer capacitive moisture sensitive element is exposed to a high temperature and a high humidity, an organic solvent atmosphere, cigarette smoke or a gas, or the like, the actual characteristics of the element drift from adjusted characteristics (a shift in characteristics of a moisture sensitive film). Once the characteristics drift, it takes much time to restore the original characteristics.

If the moisture sensitive element whose characteristics have drifted in this manner is replaceable, the element itself may be replaced with another element. Otherwise, an oscillator including an adjusted moisture sensitive element must be replaced.

In addition, an oscillator which includes an adjusting trimmer needs to be adjusted in situ by referring to an Assmann draft gage.

The replacement of a moisture sensitive element or an oscillator including a moisture sensitive element requires extra expenditure. Furthermore, such readjustment in situ by means of an Assmann draft gage demands an adjustment cost, and poses a problem in terms of adjustment precision.

SUMMARY OF THE INVENTION

It is an object of the present invention to provide a moisture sensitive device which is capable of restoring the original characteristics thereof in a short time without necessity of replacing and readjusting the device or a circuit including the device in situ.

In order to achieve the above object, according to the present invention, there is provided a moisture sensitive device comprising a polymer capacitive moisture sensitive element formed by sequentially stacking a lower electrode, a moisture sensitive film made of an organic polymer resin material, and an upper electrode on an insulating substrate, and heating means for heating the moisture sensitive film.

BRIEF DESCRIPTION OF THE DRAWINGS

FIGS. 5A and 5B are a perspective view and a plan view, respectively, showing a moisture sensitive device according to another embodiment of the present invention;

FIGS. 29A to 29C are sectional views, respectively, showing a moisture sensitive device according to still another embodiment of the present invention.

DESCRIPTION OF THE PREFERRED EMBODIMENTS

Embodiments of the present invention will be described in detail below with reference to the accompanying drawings.

Figure 1:
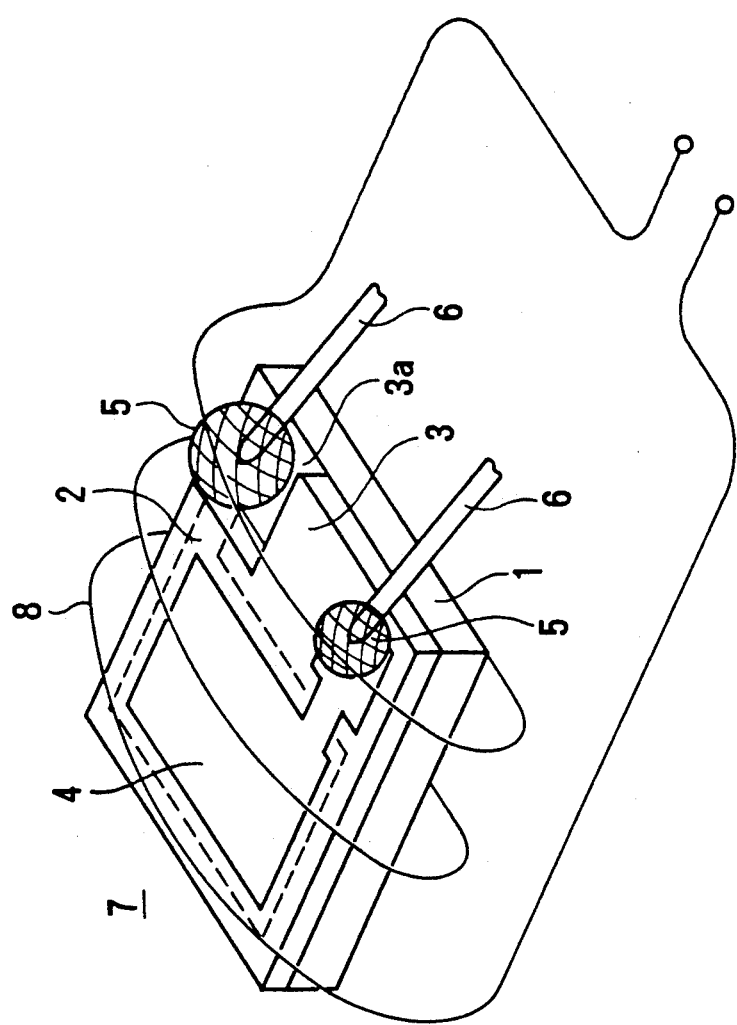
FIG. 1 is a perspective view showing the arrangement of a moisture sensitive device according to an embodiment of the present invention.

FIG. 1 shows the arrangement of a moisture sensitive device according to an embodiment of the present invention. Referring to FIG. 1, reference numeral 1 denotes a square insulating substrate made of alumina, glass, a thermal silicon oxide, or the like; 2, a lower electrode consisting of platinum or the like and formed on the upper surface of the insulating substrate 1; and 3, a moisture sensitive film (hereinafter referred to as a moisture sensitive film) coated on the lower electrode 2 by, e.g., spin coating or dipping organic polymer resin. The moisture sensitive film 3 is made of a moisture sensitive material such as cellulose, acetate, butyrate, polyimide, or acrylic resin. Reference numeral 4 denotes an upper electrode made of, e.g., gold, and formed on the moisture sensitive film 3. One of the four corners of the moisture sensitive film 3 is notched such that part of the lower electrode 2 is exposed on the insulating substrate 1 at a position corresponding to the notched portion 3a.

The moisture sensitive film 3 is sandwiched between the lower and upper electrodes 2 and 4, and lead wires 6 are respectively connected to the lower and upper electrodes 2 and 4 to detect a change in capacitance corresponding to the relative humidity of the moisture sensitive film 3. The lead wires 6 are electrically connected to the lower electrode 2 and the upper electrode 4, respectively, through electrode extraction portions 5 made of, e.g., an acrylic- or epoxy-based conductive resin, thereby forming a polymer capacitive moisture sensitive element 7.

In addition, a heater 8 for heating at least the moisture sensitive film 3 is wound around this polymer capacitive moisture sensitive element 7. The heater 8 is made of, e.g., a nichrome wire or a platinum wire, and has a timer and the like (not shown) connected as external units.

Figure 2:
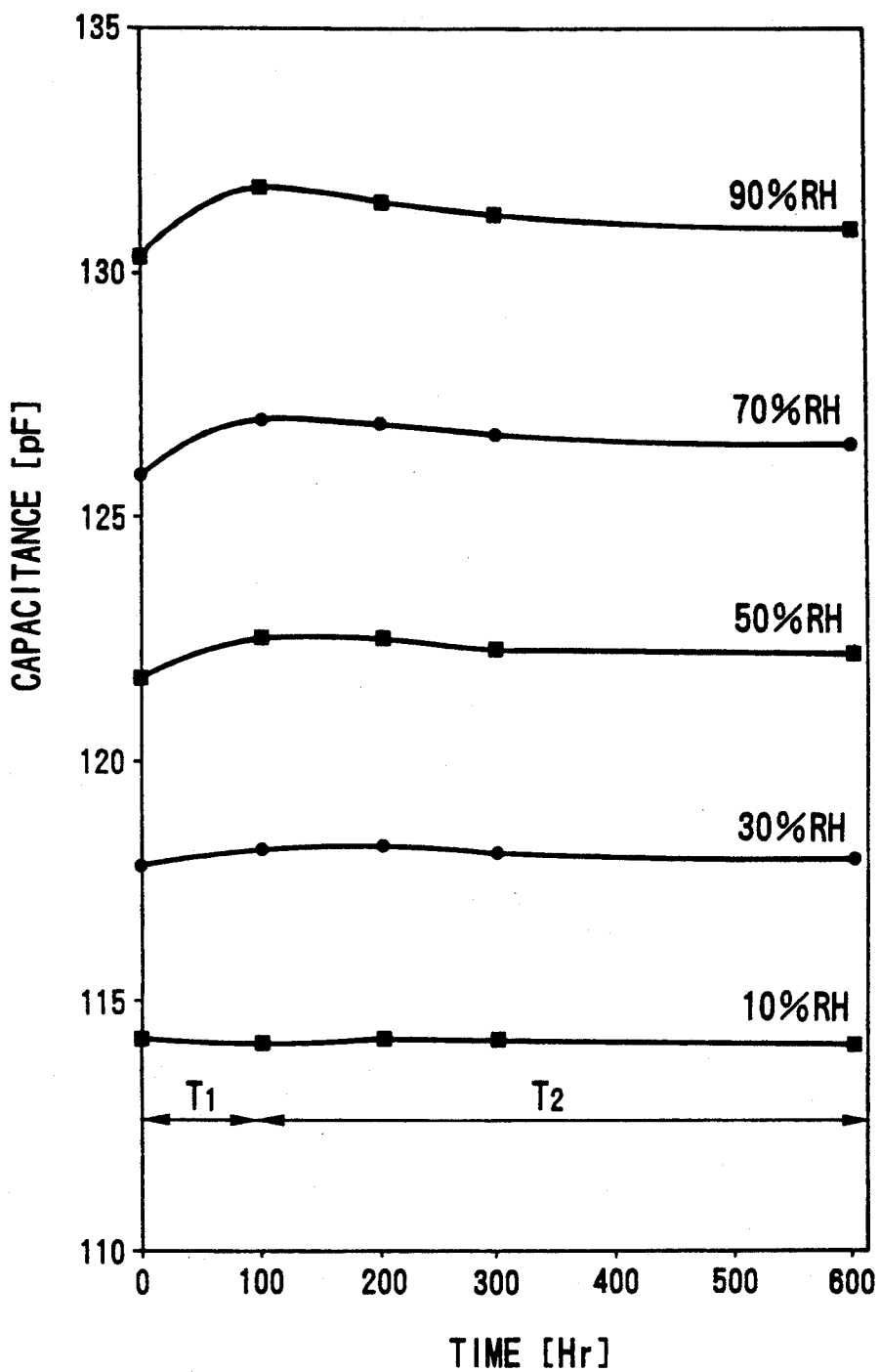
FIG. 2 is a graph showing the capacitance characteristics of a conventional moisture sensitive element.

FIG. 2 shows changes in capacitance of a conventional moisture sensitive element having no heating means in a case wherein the element is kept in an indoor atmosphere of normal temperature and normal humidity for 500 hours after it is kept at a constant temperature of 40° C. and a constant humidity of 90%RH for 100 hours. Referring to FIG. 2, reference symbol $T_1$ denotes the time interval between 0 and 100 hours, during which the moisture sensitive element is kept at 40° C. and 90%RH; and $T_2$, the time interval between 100 and 600 hours, during which the element is kept in the indoor atmosphere of normal temperature and normal humidity. Referring to FIG. 2, the characteristic curves associated with 10%RH, 30%RH, 50%RH, 70%RH, and 90%RH respectively indicate changes in capacitance at 25° C. and the respective relative humidities.

As is apparent from FIG. 2, if the conventional moisture sensitive element is kept at 40° C. and 90%RH for 100 hours, its capacitance drifts toward the positive side. Afterward, even if the element is kept at normal temperature and normal humidity for 500 hours, the characteristics set before the element was kept at 40° C. and 90%RH cannot be completely restored.

As described above, exposure of a moisture sensitive element for a long time to a high-temperature and high-humidity state, an organic solvent atmosphere, or cigarette smoke, or the like, may result in drift of the outputted capacitance value from an initial value which has been adjusted at the time of shipment. Furthermore, it takes much time to restore the characteristics once drifted. For this reason, an element or an oscillator including an element needs to be replaced. Alternatively, readjustment must be performed in situ by using an Assmann draft gage.

The present invention is designed to restore initial characteristics (capacitance) of a moisture sensitive element, which have drifted due to a high-temperature and high-humidity state, an organic solvent atmosphere, cigarette smoke, or the like, within a short period of time by heating, thereby eliminating the necessity for replacement of the element or readjustment in situ.

Effects obtained by the moisture sensitive device according to this embodiment of the present invention will be described next.

Figure 3:
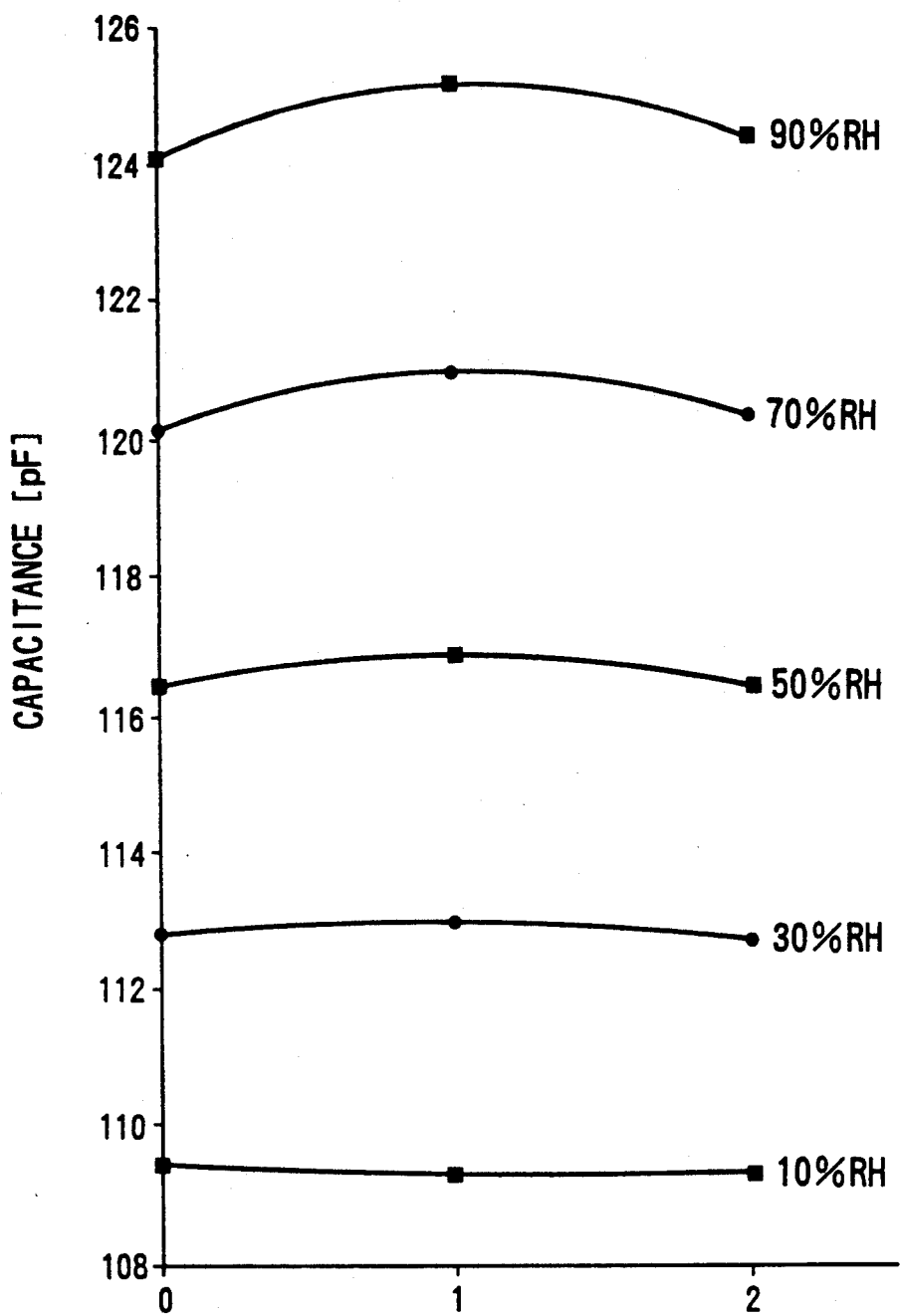
FIG. 3 is a graph showing the capacitance characteristics of a moisture sensitive element according to the present invention.

FIG. 3 shows characteristics (capacitance) of the moisture sensitive element 7 having the heater shown in FIG. 1 in a case wherein the element is kept in a tank at a constant temperature of 40° C. and a constant humidity of 90%RH for 100 hours, and the element is heated at 90° C. (normal temperature) for 20 minutes. Referring to FIG. 3, "0" on the abscissa corresponds to the initial characteristics; "1", the characteristics obtained after the element was kept at 40° C. and 90%RH for 100 hours; and "2", the characteristics obtained after the element was subsequently heated at 90° C. for 20 minutes.

As is apparent from FIG. 3, the initial characteristics can be substantially restored by heating the element at 90° C. for 20 minutes.

Figure 4:
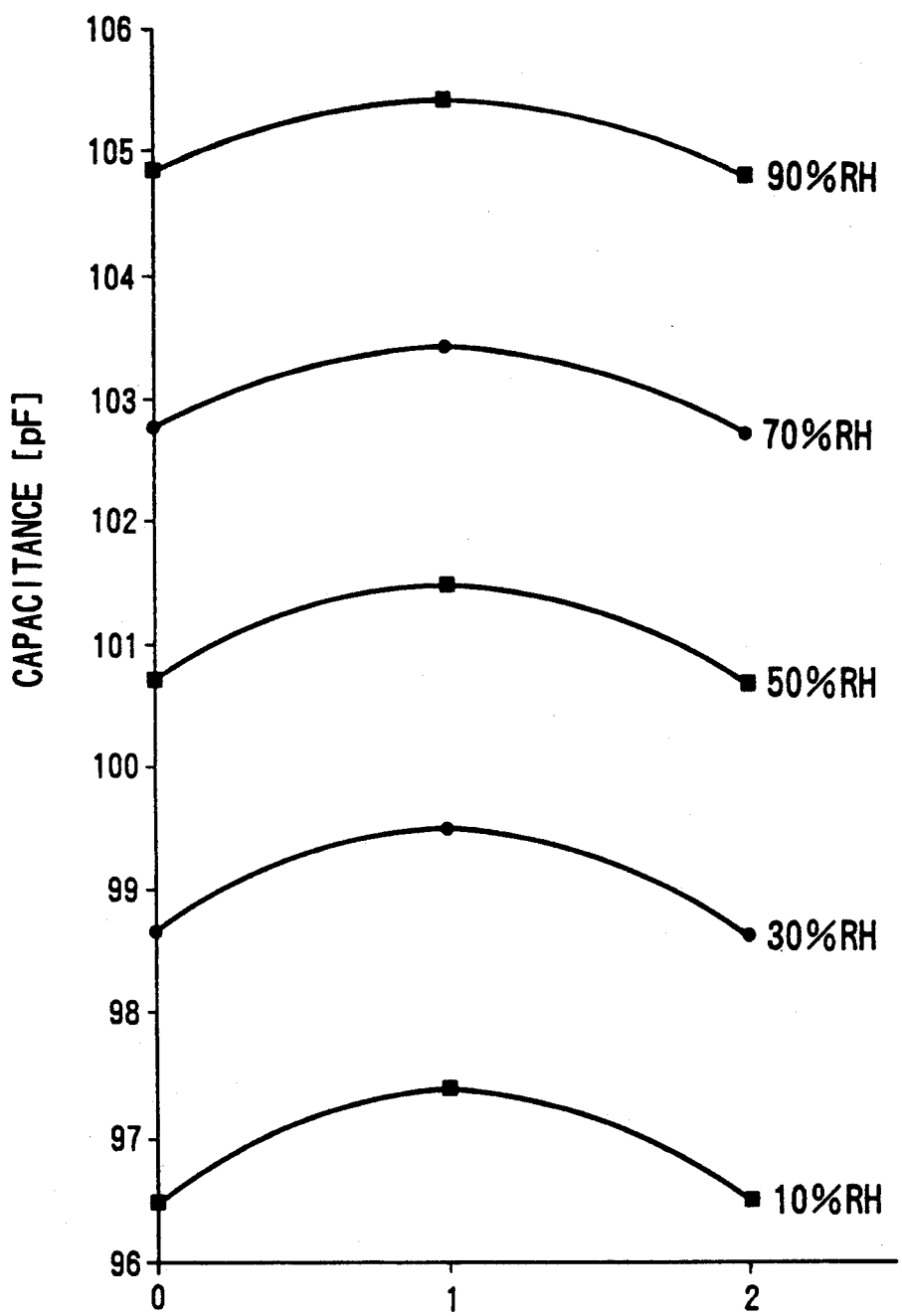
FIG. 4 is a graph showing the capacitance characteristics of the moisture sensitive element according to the present invention, which are obtained when the element is kept in an organic solvent.

FIG. 4 shows a case wherein the characteristics of the moisture sensitive element 7 are measured after the element 7 was kept in a saturated vapor of acetone as an organic solvent for 20 minutes, and the characteristics are measured again after the element 7 was heated at 100° C. for one hour. Referring to FIG. 4, "0" on the abscissa corresponds to the initial characteristics of the moisture sensitive element 7; "1", the characteristics obtained after the element 7 was kept in the acetone saturated vapor for 20 minutes; and "2", the characteristics obtained after the element was heated at 100° C. for one hour.

As is apparent from FIG. 4, the initial characteristics can be almost completely restored by heating the moisture sensitive element 7 at 100° C. for one hour.

According to this arrangement, the characteristics of the moisture sensitive element 7 which have drifted can be restored to the original state by heating the element 7, thus ensuring long-term stability of the element 7.

Note that if heating is performed at a high temperature below the softening point or glass transition point of the polymer, the initial characteristics can be restored within a shorter heating time.

FIG. 5A shows a moisture sensitive element according to another embodiment of the present invention. FIG. 5B is a plan view of the moisture sensitive element. The arrangement shown in FIGS. 5A and 5B is different from that shown in FIG. 1 in that notched portions 3a are formed at two corners on one of the diagonals of a moisture sensitive film 3, one lead wire 6a is connected to an upper electrode 4, and two lead wires 6b and 6c are respectively connected to portions of a lower electrode 2, thereby forming a moisture sensitive element 701.

Figure 6:
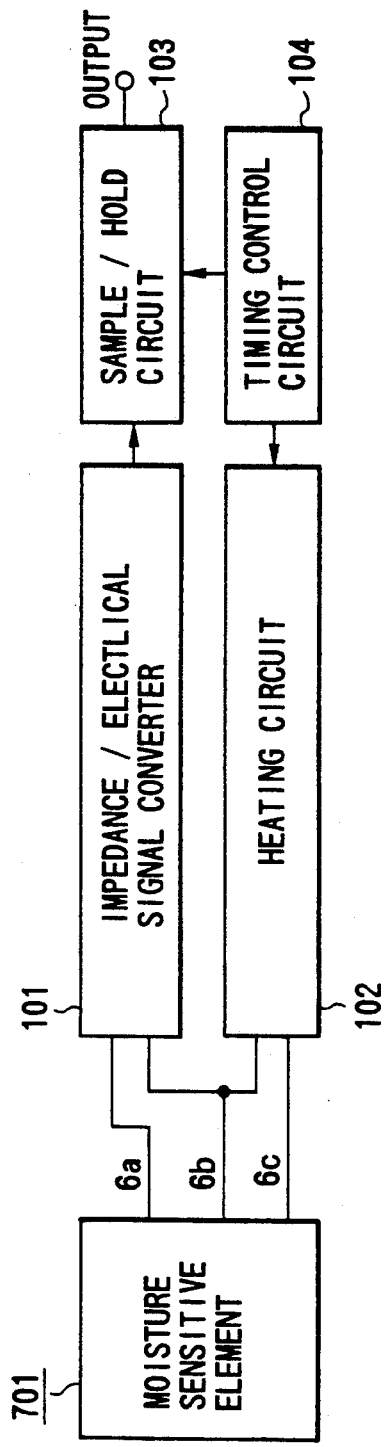
FIG. 6 is a block diagram showing a driving circuit for operating the moisture sensitive device in FIGS. 5A and 5B.

A signal is obtained from the moisture sensitive element 701 having the above-described arrangement by the driving circuit shown in FIG. 6. More specifically, the lead wires 6a and 6b of the moisture sensitive element 701 are connected to an impedance/electrical signal converter 101 to obtain humidity information. In addition, the lead wires 6b and 6c are connected to a heating circuit 102 to supply a current to the lower electrode 2 so as to generate heat, thus heating the moisture sensitive element 701. During a heating/cooling operation, an output value obtained from the moisture sensitive element 701 immediately before the operation is held by a sample/hold circuit 103, and the held value is output. The timing of the sample/hold circuit 103 and the heating circuit 102 is controlled by a timing controller 104.

Note that the above-described arrangement may be modified such that the moisture sensitive element 701 is continuously heated by the heating circuit 102 to be constantly operated in a high-temperature state. In this case, the sample/hold circuit 103 and the timing controller 104 are not required. The heating temperature is controlled by utilizing the temperature dependency characteristic of the resistivity of a conductor.

Figure 7:
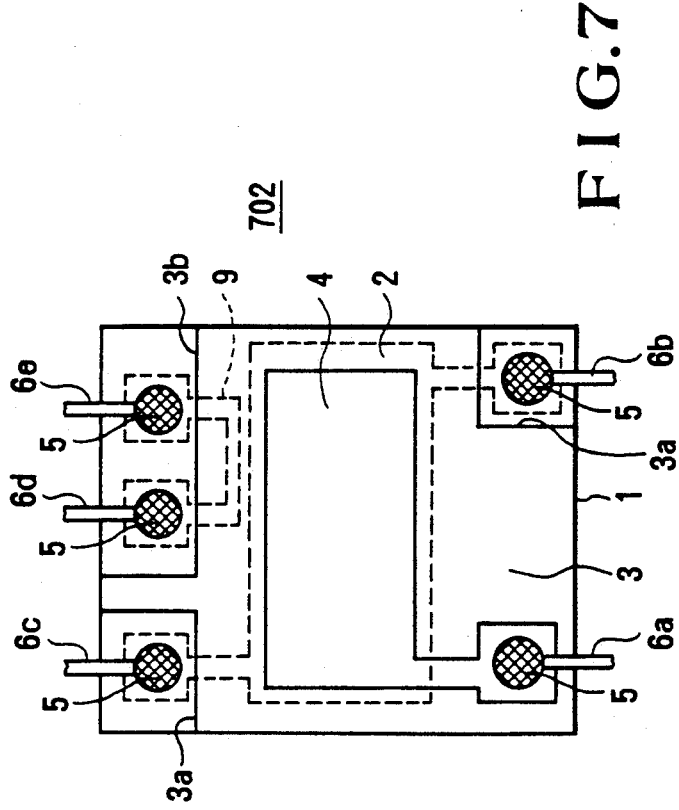
FIG. 7 is a plan view showing a moisture sensitive device according to still another embodiment of the present invention.

FIG. 7 shows a moisture sensitive element according to still another embodiment of the present invention. The arrangement shown in FIG. 7 is different from that shown in FIGS. 5A and 5B in that a relatively large notched portion 3b is formed at a third corner of a moisture sensitive film 3, a temperature measuring resistor 9 is arranged between an insulating substrate 1 and the moisture sensitive film 3, and lead wires 6d and 6e are connected to the two ends of the temperature measuring resistor 9, thereby forming a moisture sensitive element 702.

Figure 8:
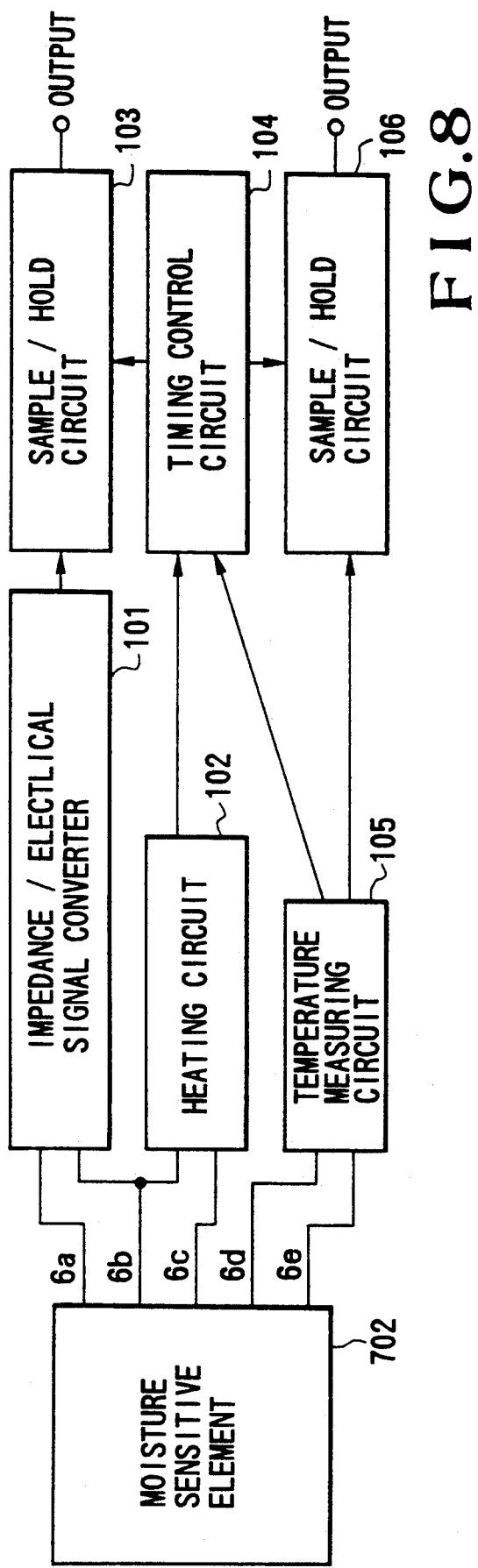
FIG. 8 is a block diagram showing a driving circuit for operating the moisture sensitive device in FIG. 7.
Figure 9:
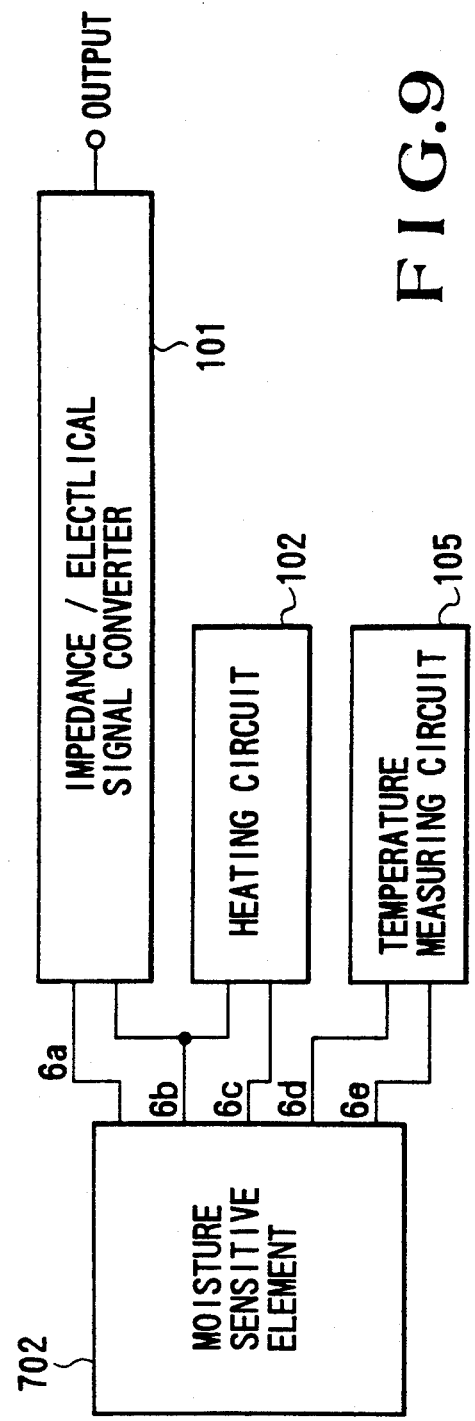
FIG. 9 is a block diagram showing a driving circuit for operating the moisture sensitive device in FIG. 7.

This arrangement allows the single sensor to simultaneously output information and temperature information. As shown in FIG. 8 illustrating a driving circuit for the moisture sensitive element 702, the lead wires 6d and 6e are connected to a temperature measuring circuit 105, and a heating circuit 102 is controlled by using an output from the temperature measuring circuit 105 so that heating and cooling operations can be performed at optimal temperatures. By supplying an output from the temperature measuring circuit 105 to a timing controller 104, an output value after a cooling operation can be immediately output, whereby the cooling time can be shortened. It is further possible to prevent the output from the humidity sensitive element 702 while it is not sufficiently cooled. The moisture sensitive element 702 may be continuously operated at a high temperature by using the driving circuit shown in FIG. 9. In this case, since a high temperature is constantly set, and no timing control is required, sample/hold circuits 103 and 106 and the timing controller 104 can be omitted.

Figure 10:
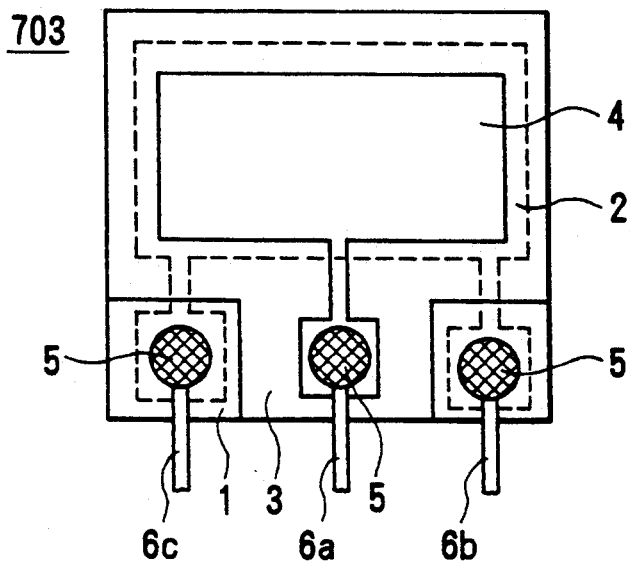
FIG. 10 is a plan view showing a moisture sensitive device according to still another embodiment of the present invention.

FIG. 10 shows a moisture sensitive element according to still another embodiment of the present invention. The arrangement shown in FIG. 10 is different from that shown in FIGS. 5A and 5B in that a moisture sensitive element 703 has lead wires 6a, 6b, and 6c led out from the same side.

Figure 11:
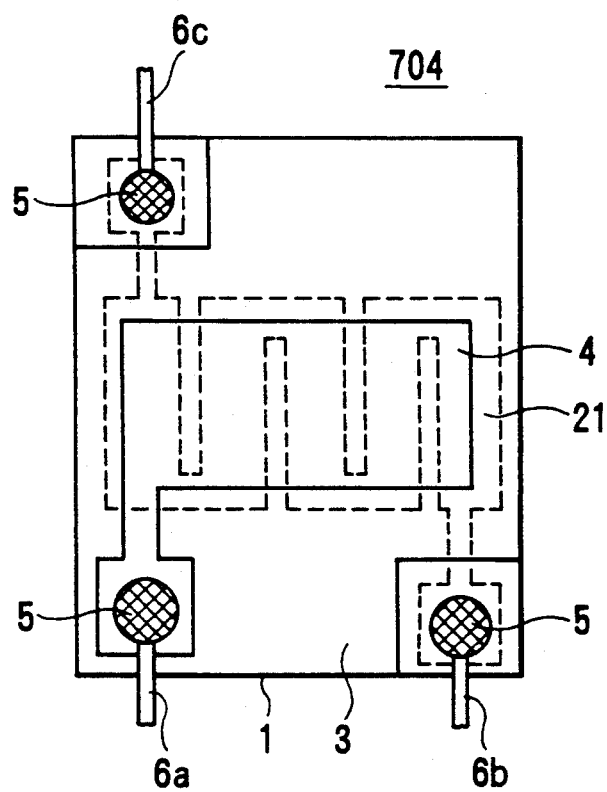
FIG. 11 is a plan view showing a moisture sensitive device according to still another embodiment of the present invention.

FIG. 11 shows a moisture sensitive element according to still another embodiment of the present invention. The arrangement shown in FIG. 11 is different from that shown in FIGS. 5A and 5B in that a lower electrode 21 is patterned in a zigzag shape to form a moisture sensitive element 704.

According to this arrangement, when a current flows between lead wires 6b and 6c, no current density difference is generated and heating can be performed uniformly.

Figure 12:
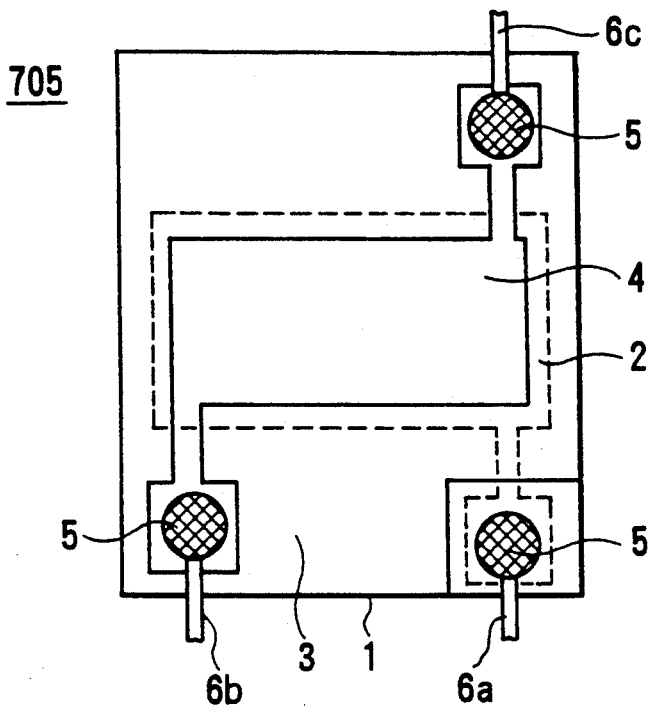
FIG. 12 is a plan view showing a moisture sensitive device according to still another embodiment of the present invention.

FIG. 12 shows a moisture sensitive element according to still another embodiment of the present invention. The arrangement shown in FIG. 12 is different from that shown in FIGS. 5A and 5B in that a moisture sensitive element 705 is designed such that two lead wires 6b and 6c are formed not on a lower electrode 2 but on an upper electrode such that the upper electrode 4 is used as a heating electrode. Alternatively, the two lead wires 6b and 6c may be taken out from two opposite sides of the upper electrode 4.

Figure 13:
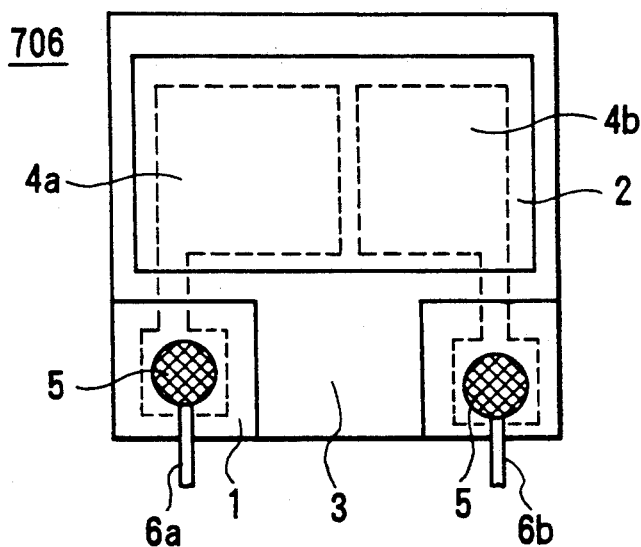
FIG. 13 is a plan view showing an arrangement of a moisture sensitive element.
Figure 14:
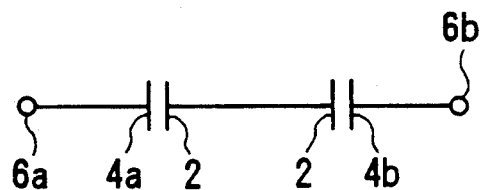
FIG. 14 is a circuit diagram showing the equivalent circuit of the moisture sensitive element in FIG. 13.

FIG. 13 shows an arrangement of a moisture sensitive element. In a moisture sensitive element 706 thus constructed, an upper electrode 4 is constituted by two divided electrodes, i.e., a first upper electrode 4a and a second upper electrode 4b. FIG. 14 shows the equivalent circuit of the moisture sensitive element 706, in which two capacitors, respectively constituted by the upper electrodes 4a and 4b and lower electrodes 2, are connected in series.

Figure 15:
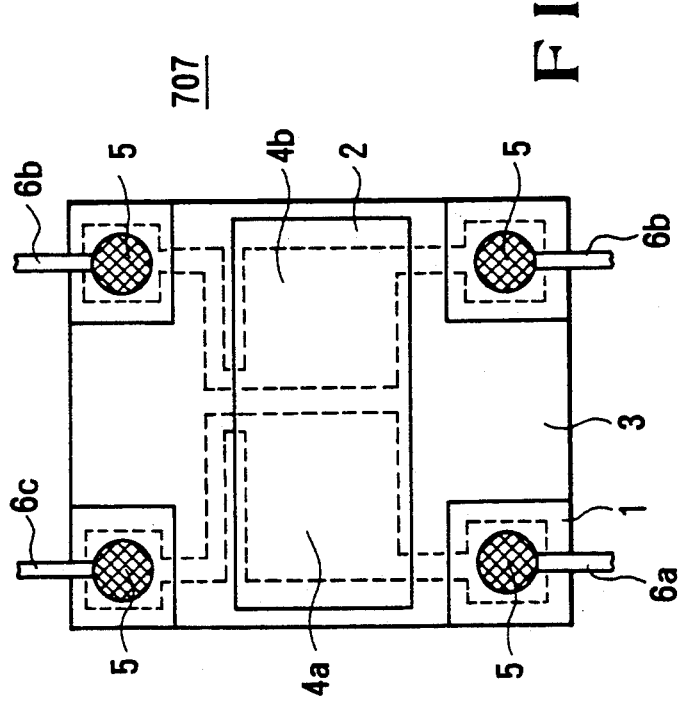
FIG. 15 is a plan view showing a moisture sensitive device according to still another embodiment of the present invention.

FIG. 15 shows an embodiment in which the embodiment described with reference to FIGS. 5A and 5B is applied to the moisture sensitive element shown in FIG. 13. Referring to FIG. 15, a lead wire 6c is taken out from a first upper electrode 4a, and a lead wire 6d from a second upper electrode 4b, thereby forming a moisture sensitive element 707.

Figure 16:
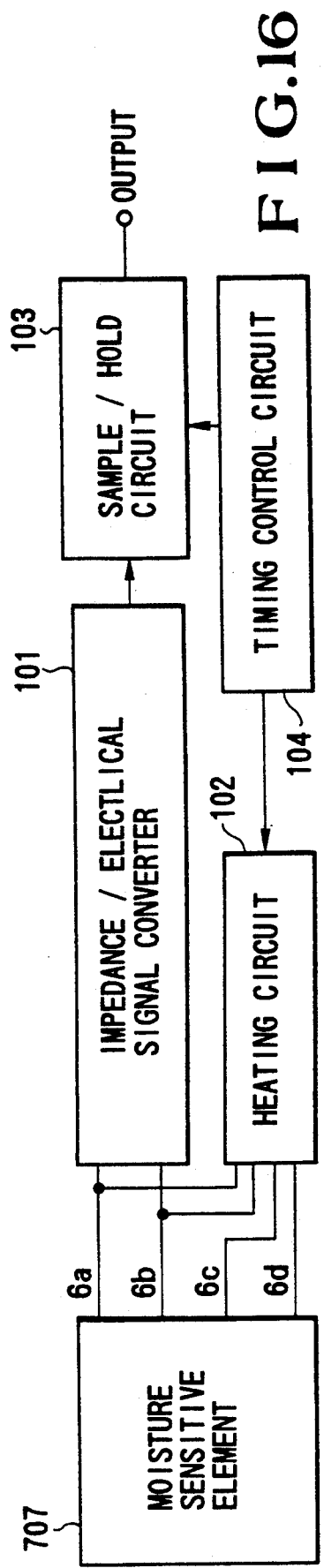
FIG. 16 is a block diagram showing a driving circuit for operating the moisture sensitive device in FIG. 15.

According to this arrangement, a moisture sensitive film 3 can be heated by supplying currents between the lead wires 6a and 6c and between the lead wires 6b and 6d, respectively. A driving circuit for this moisture sensitive element can be realized by the one shown in FIG. 16.

Figure 17:
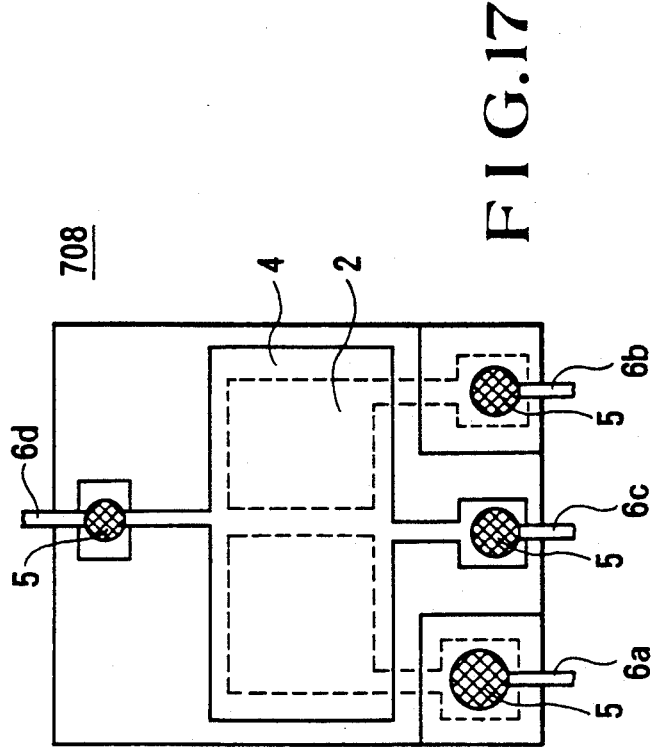
FIG. 17 is a plan view showing a moisture sensitive device according to still another embodiment of the present invention.

FIG. 17 shows a modification of the embodiment described with reference to FIG. 15. Referring to FIG. 17, a moisture sensitive element 708 has lead wires 6c and 6d taken out from two opposite ends of an upper electrode 4.

Figure 18:
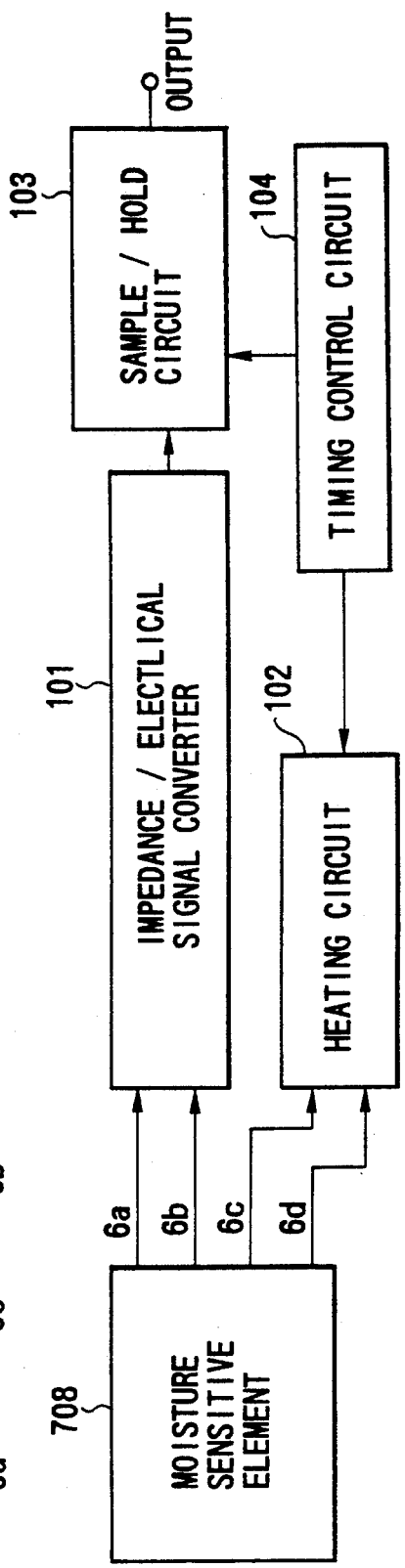
FIG. 18 is a block diagram showing a driving circuit for operating the moisture sensitive device in FIG. 17.

According to this arrangement, a moisture sensitive film 3 can be heated by supplying a current between the lead wires 6c and 6d. A driving circuit for the moisture sensitive element 708 can be realized by the one shown in FIG. 18.

Figure 19:
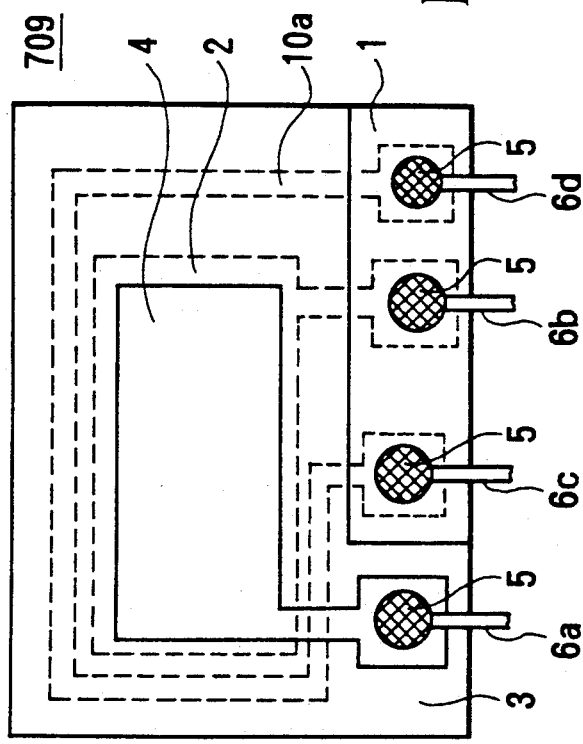
FIG. 19 is a plan view showing a moisture sensitive device according to still another embodiment of the present invention.

FIG. 19 shows a modification of the embodiment described with reference to FIGS. 5A and 5B. Referring to FIG. 19, a heater 10a is formed on the same plane of an insulating substrate 1 on which a lower electrode 2 is formed so as to surround the lower electrode 2, and lead wires 6c and 6d are taken out from the two opposite ends of the heater 10a, thereby forming a moisture sensitive element 709. Two lead wires out of the four may be integrated into one lead wire so as to form a total of three lead wires.

Figure 20:
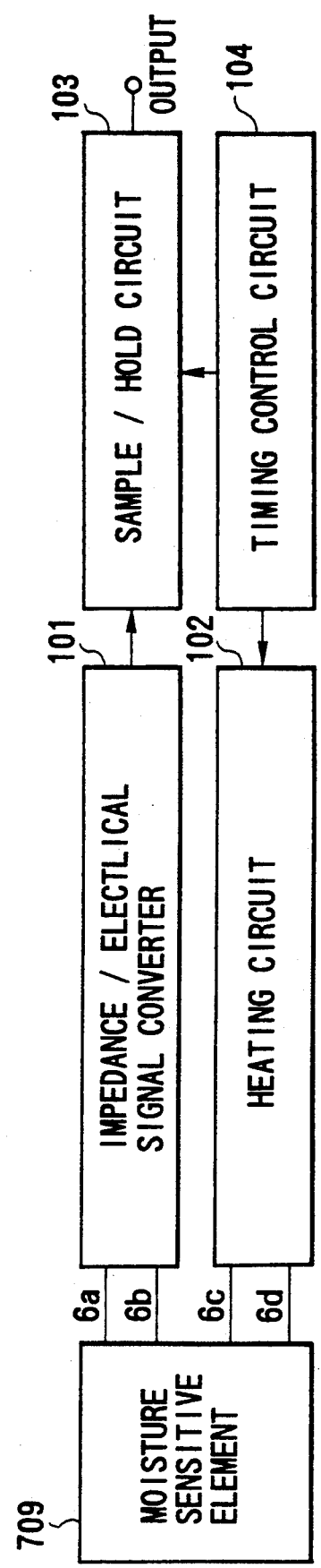
FIG. 20 is a block diagram showing a driving circuit for operating the moisture sensitive device in FIG. 19.

According to this arrangement, a moisture sensitive film 3 can be heated by supplying a current between the lead wires 6c and 6d. A driving circuit for the moisture sensitive element 709 can be realized by the one shown in FIG. 20.

Figure 21:
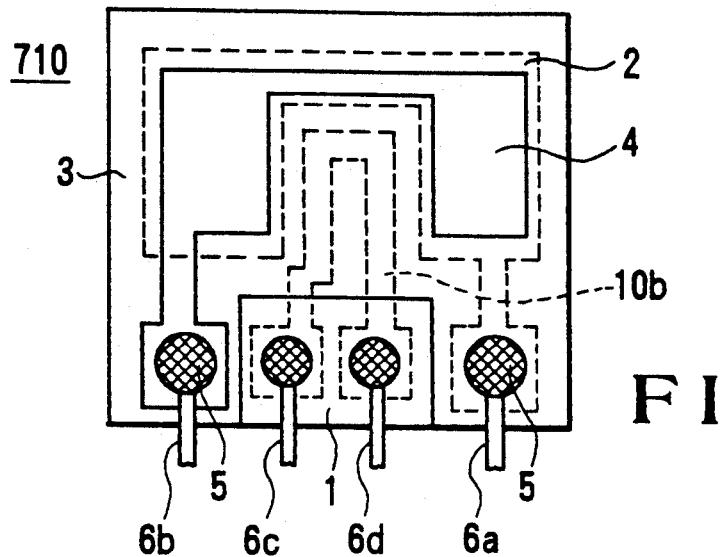
FIG. 21 is a plan view showing a moisture sensitive device according to still another embodiment of the present invention.

FIG. 21 shows a modification of the embodiment described with reference to FIG. 19. Referring to FIG. 21, a heater 10b is arranged inside lower and upper electrodes 2 and 4, and lead wires 6c and 6d are taken out from the two ends of the heater 10b, thereby forming a moisture sensitive element 710.

According to this arrangement, a moisture sensitive film 3 can be heated from a portion located inside from the lower and upper electrodes 2 and 4 by supplying a current between the lead wires 6c and 6d. Alternatively, the moisture sensitive film 3 may be simultaneously heated from portions located inside and outside the lower and upper electrodes 2 and 4. Note that a driving circuit for the moisture sensitive element 710 can be realized by the one shown in FIG. 20.

Incidentally, each of the embodiments shown in FIGS. 15, 17, 19, and 21 may include the temperature measuring resistor 9 in FIG. 7.

Figure 22:
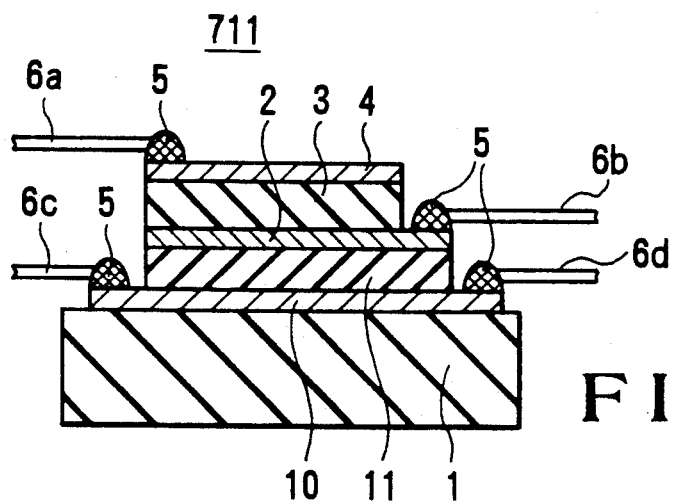
FIG. 22 is a sectional view showing a moisture sensitive device according to still another embodiment of the present invention.

FIG. 22 shows a modification of the embodiment shown in FIG. 19. Referring to FIG. 22, a heater 10 is formed on almost the entire surface of an insulating substrate 1 made of glass or the like. An insulating film 11 is formed on the heater 10, and a lower electrode 2, a moisture sensitive film 3, an upper electrode 4, and the like are subsequently stacked thereon, thereby forming a moisture sensitive element 711.

Figure 23:
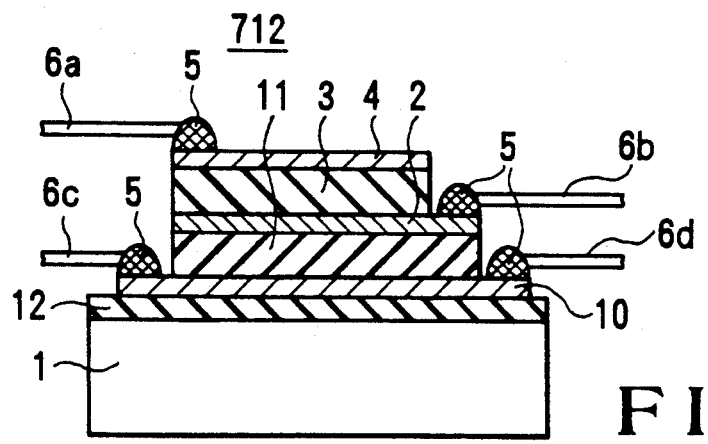
FIG. 23 is a sectional view showing a moisture sensitive device according to still another embodiment of the present invention.

FIG. 23 shows a modification of the structure shown in FIG. 22. Referring to FIG. 23, an insulating substrate 1 is made of a conductive material such as a metal or semiconductor material, and an insulating film 12 is formed between a heater 10 and the insulating substrate 1, thereby forming a moisture sensitive element 712.

In the above-described embodiment, the moisture sensitive element 712 has the heater 10 formed immediately below the moisture sensitive film 3. However, the heater 10 may be formed on the lower surface side of the insulating substrate 1.

Figure 24A:
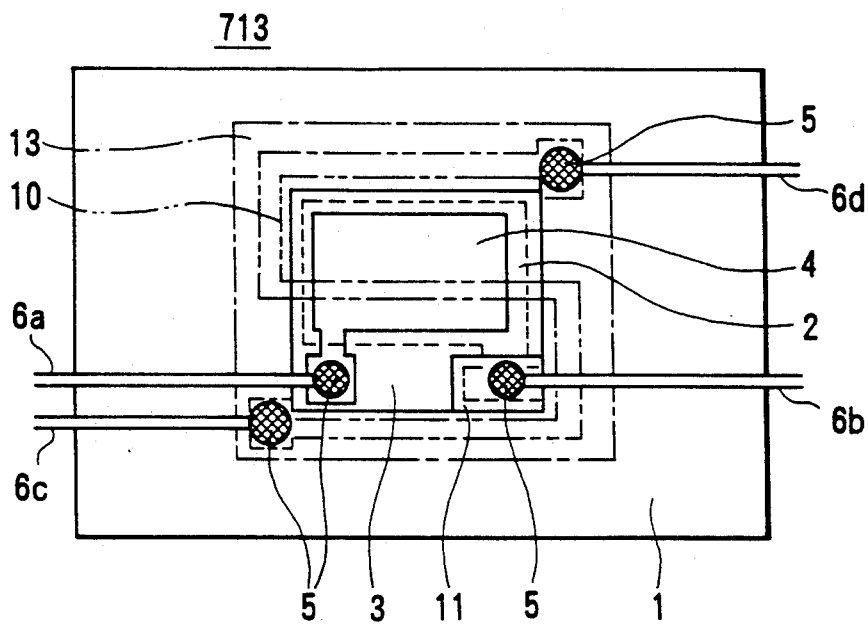
FIGS. 24A and 24B are a plan view and a sectional view, respectively, showing a moisture sensitive device according to still another embodiment of the present invention.
Figure 24B:
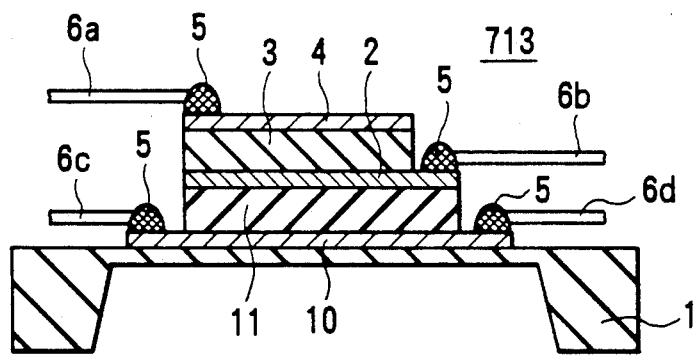
Figure 25:
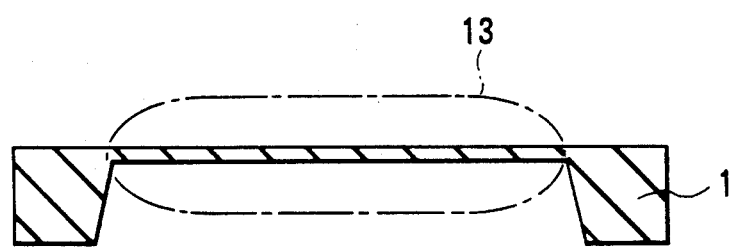
FIG. 25 is a sectional view showing the arrangement of a diaphragm portion.

FIGS. 24A and 24B show a modification of the structure shown in FIG. 22. FIG. 24A is a plan view of the modification. FIG. 24B is a sectional view of the modification. Referring to FIGS. 24A and 24B, a heater 10, a lower electrode 2, a moisture sensitive film 3, and a lower electrode 4 are formed on a diaphragm 13 formed on an insulating substrate 1 shown in FIG. 25, thereby forming a moisture sensitive element 713. Note that the insulating substrate 1 is made of glass.

According to this arrangement, the heater 10, the lower electrode 2, the moisture sensitive film 3, and the upper electrode 4 stacked on the diaphragm 13 are thermally insulated from other portions of the insulating substrate 1 so that their response speeds in heating and cooling operations are increased, which result in reduced power consumption of the heater 10. The diaphragm 13 shown in FIG. 25 can be formed by a grinding method of mechanically grinding the insulating substrate 1 from its lower surface side, a chemical etching method, a dry etching method such as plasma etching, or the like.

Figure 26A:
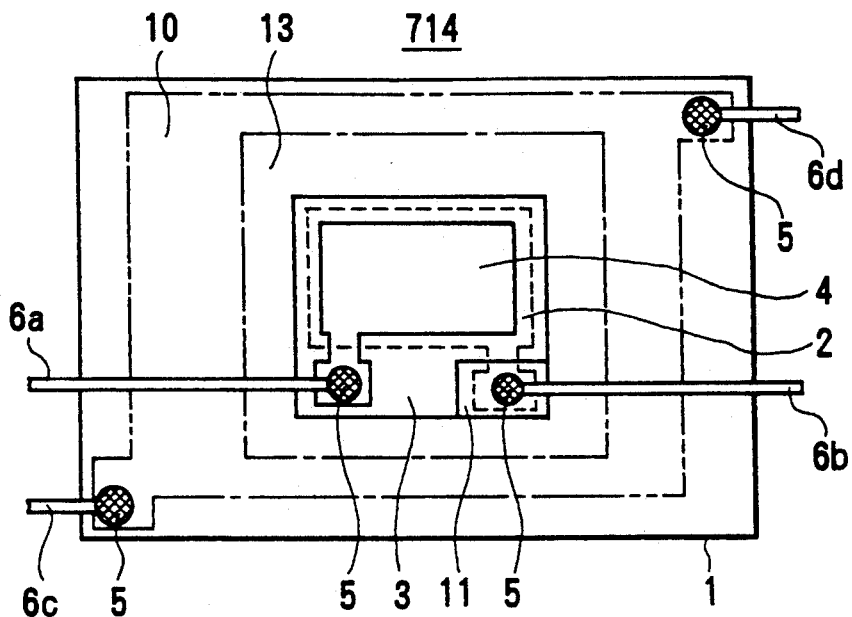
FIGS. 26A to 26D are a plan view and sectional views, respectively, showing a moisture sensitive device according to still another embodiment of the present invention.
Figure 26B:
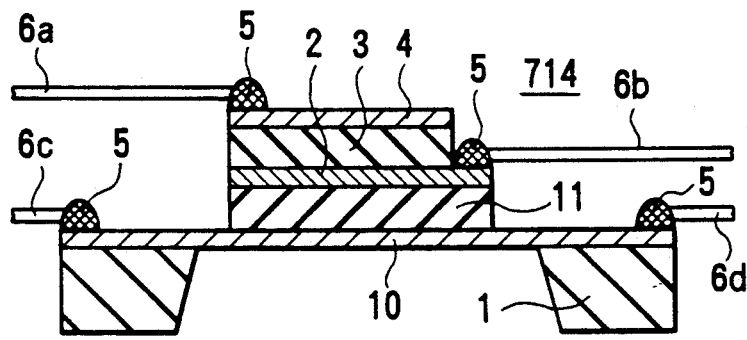
Figure 26C:
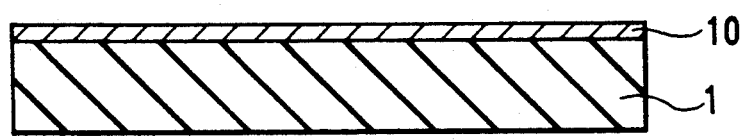
Figure 26D:
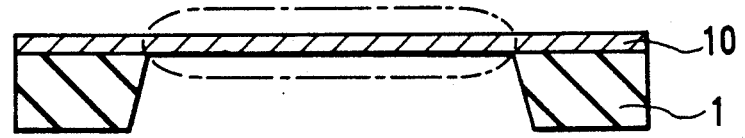

FIGS. 26A to 26D show a modification of the structure shown in FIGS. 24A and 24B. FIG. 26A is a plan view of the modification. FIG. 26B is a sectional view of the modification. FIGS. 26C and 26D show the manufacturing steps. The structure shown in FIGS. 26A and 26B is different from that shown in FIGS. 24A and 24B in the arrangement of a diaphragm 13. More specifically, as shown in FIG. 26C, a heater 10 is formed on an insulating substrate 1, and a portion of the substrate 1 is removed from its lower surface side by one of the etching methods described above. As shown in FIG. 26D, the diaphragm 13 is constituted by the heater 10, thereby forming a moisture sensitive element 714.

Figure 27A:
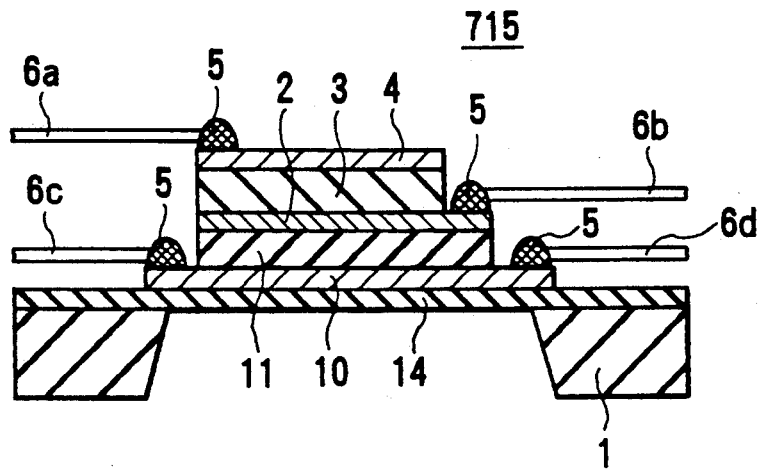
FIGS. 27A to 27C are sectional views, respectively, showing a moisture sensitive device according to still another embodiment of the present invention.
Figure 27B:
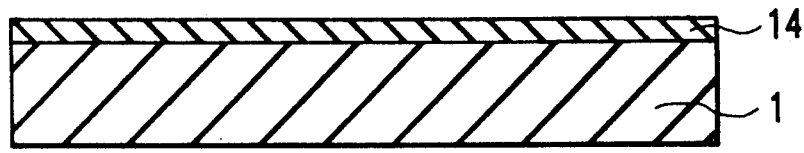
Figure 27C:
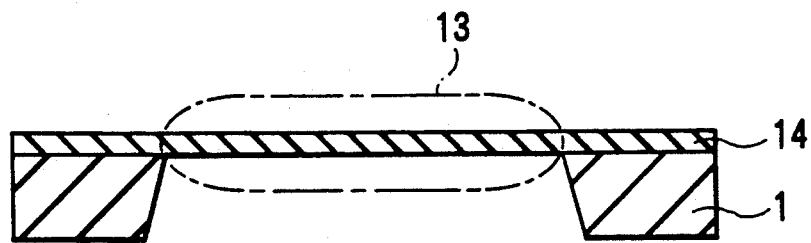

FIGS. 27A to 27C show a modifications of the structure shown in FIGS. 24A and 24B. FIG. 27A is a sectional view of the modification. FIGS. 27B and 27C show the manufacturing steps. The structure shown in FIG. 27A is different from that shown in FIGS. 24A and 24B in that an etching stop layer 14 is formed on the upper surface of an insulating substrate 1. As shown in FIG. 27C, a portion of the insulating substrate 1 is removed from its lower surface side by one of the etching methods described above, and a diaphragm 13 is constituted by the etching stop layer 14, thereby forming a moisture sensitive element 715.

According to this arrangement, since the etching stop layer 14 allows the insulating substrate 1 to be etched at a higher speed.

Figure 28A:
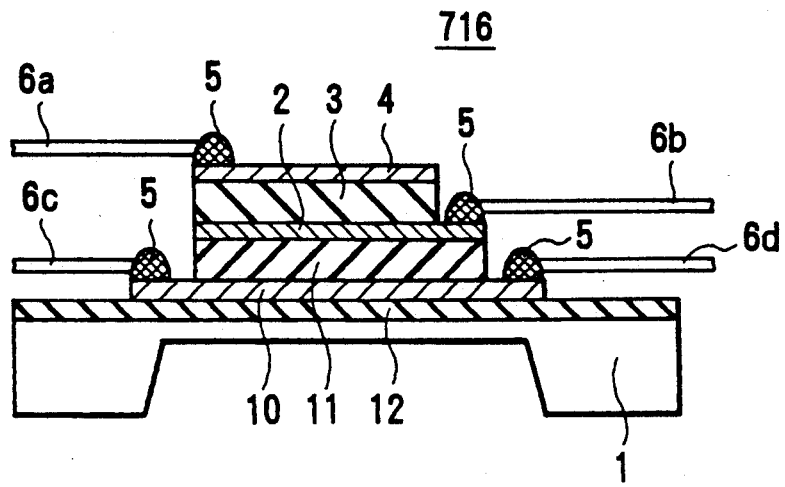
FIGS. 28A to 28C are sectional views, respectively, showing a moisture sensitive device according to still another embodiment of the present invention.
Figure 28B:
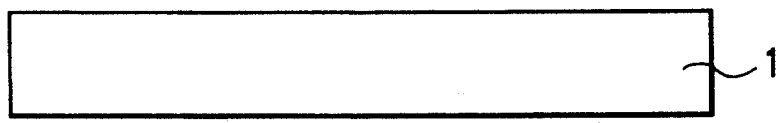
Figure 28C:
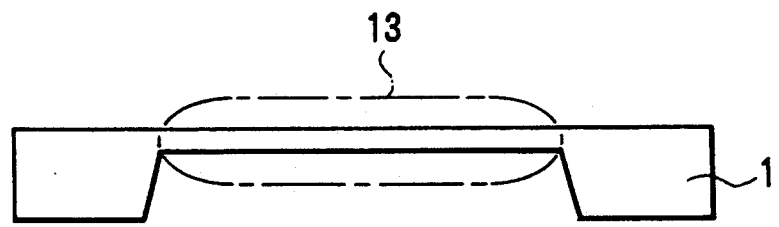

FIGS. 28A to 28C show a modification of the structure shown in FIGS. 24A and 24B. FIG. 28A is a sectional view of the modification. FIGS. 28B and 28C show the manufacturing steps. Referring to FIG. 28A, an insulating substrate 1 is made of a conductive material such as a metal or semiconductor material. In this case, a portion of the insulating substrate 1 shown in FIG. 28B is removed by one of the etching methods described above to form a diaphragm 13 shown in FIG. 28C, and an insulating film 12 is formed between the diaphragm 13 and a heater 10, thereby forming a moisture sensitive element 716.

FIGS. 29A to 29C show a modification of the structure shown in FIGS. 27A to 27C. FIG. 29A is a sectional view of the modification. FIGS. 29B and 29C show the manufacturing steps. Referring to FIG. 29A, an insulating substrate 1 is made of a conductive material such as a metal or semiconductor material. In this case, as shown in FIG. 29B, an etching stop layer 14 is formed on the insulating substrate 1. Subsequently, as shown in FIG. 29C, the insulating substrate 1 is etched from its lower surface side by one of the etching methods described above, and the etching process is stopped at the etching stop layer 14 so that a diaphragm is constituted by the etching stop layer 14, thereby forming a moisture sensitive element 717.

Figure 30A:
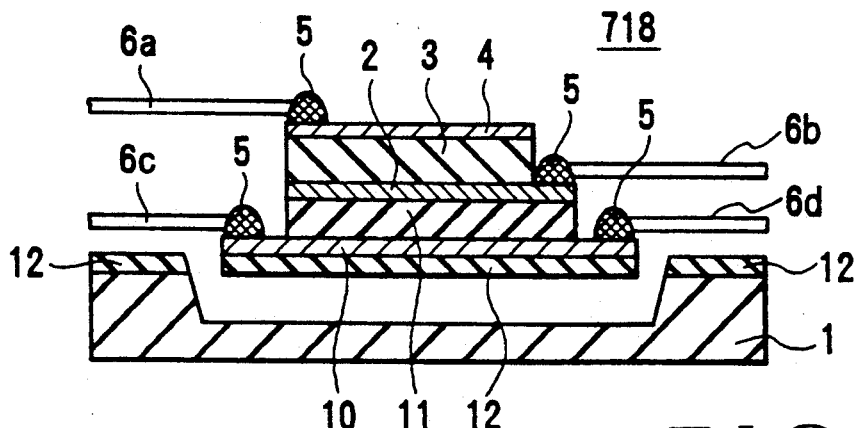
FIGS. 30A to 30D are sectional views and a perspective view, respectively, showing a moisture sensitive device according to still another embodiment of the present invention.
Figure 30B:
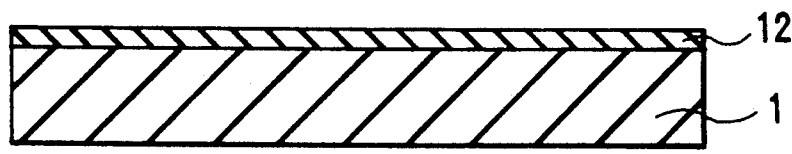
Figure 30C:
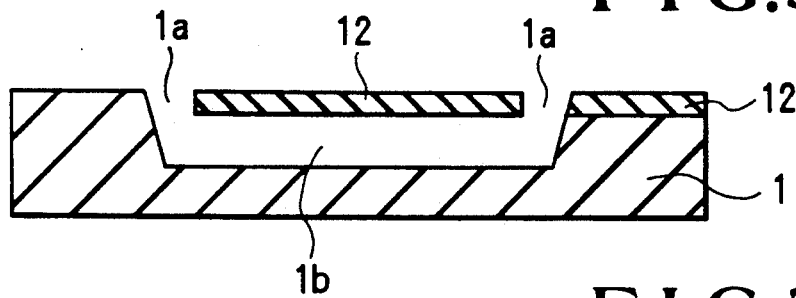
Figure 30D:
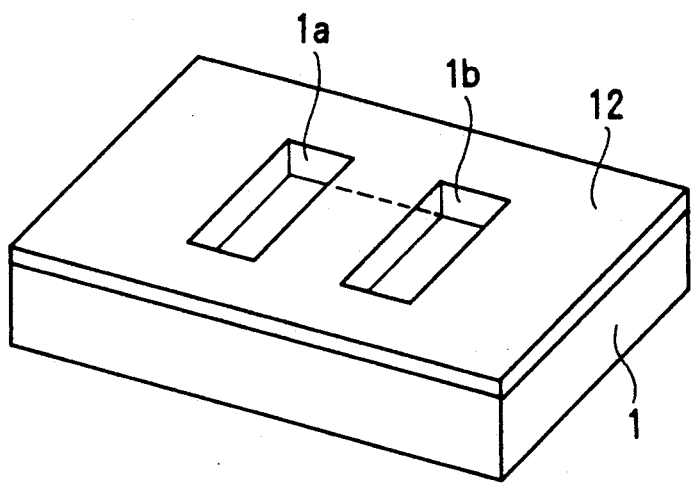

FIGS. 30A to 30D show a modification of the structure shown in FIGS. 28A to 28C. FIG. 30A is a sectional view of the modification. FIGS. 30B to 30D show manufacturing steps. Referring to FIG. 30A, a portion of an insulating substrate 1, located immediately under an insulating film 12, is etched to form a hollow portion and suspend the insulating film 12 over the hollow portion, and a heater 10, a lower electrode 2, a moisture sensitive film 3, and a lower electrode 4 are formed on the insulating film 12, thereby forming a moisture sensitive element 718. This hollow portion can be formed in the following manner. As shown in FIGS. 30C and 30D, an opening 1a is formed in a central portion of the upper surface of the insulating substrate 1, on which the insulating film 12 is formed as shown in FIG. 30B. Thereafter, a hollow portion 1b communicating with the opening 1a is formed by anisotropic etching or the like.

In each of the modifications shown in FIGS. 24A, to 24B, 26A to 26D, 27A to 27C, 28A to 28C, 29A to 29C, and 30A to 30D, the heater 10 may not be formed immediately under the lower electrode 2, the moisture sensitive film 3, and the upper electrode 4 but may be constituted by the diaphragm 13, as shown in FIGS. 19 and 21.

Furthermore, in each of the modifications shown in FIGS. 19, 21, 22, 23, 24A and 24B, 26A to 26D, 27A to 27C, 28A to 28C, 29A to 29C, and 30A to 30D, the temperature measuring resistor 9 may be arranged, as shown in FIG. 7. In this case, the temperature measuring resistor 9 may be located on the diaphragm 13, as shown in FIG. 7, or may be embedded in the insulating film 12. In addition, the heater 10 may be arranged on the lower surface side of the diaphragm 13. Furthermore, the temperature measuring resistor 9 may be formed between the insulating substrate 1 and the insulating film 12 or between the etching stop layer 14 and the insulating film 12.

The foregoing embodiments have been described for the case where a single sensor is provided. Since no output is generated during a heating operation, two sensors may be provided such that, when one of them is heated, the other one is switched to generate an output, whereby the output is continuously derived.

As has been described above, according to the present invention, since the characteristics of a polymer capacitive moisture sensitive element which have drifted can be restored to the original characteristics within a short period of time by heating, excellent long-term stability is provided. In addition, since readjustment in situ is not required, a cost associated thereto can be omitted.

What is claimed is:
1. A moisture sensitive device comprising:
   a polymer capacitive moisture sensitive element, having initial characteristics, formed by sequentially stacking, on an insulating substrate, a lower electrode, a moisture sensitive film made of an organic polymer resin material and an upper electrode; and
   heating means for heating said moisture sensitive film to restore said initial characteristics in said polymer capacitive moisture sensitive element when said characteristics drift from their initial state.
2. A device according to claim 1, wherein said heating means performs a heating operation in one of a first temperature range between the highest temperature at which said moisture sensitive device is in its normal operating condition and the temperature at which the softening commences for said moisture sensitive device, and a second temperature range between the highest temperature at which said moisture sensitive device is in its normal operating condition and the glass transition point temperature of said moisture sensitive element.
3. A device according to claim 2, wherein said heating means performs a heating operation in a temperature range between 90° C. and 200° C.

* * * * *